(12) United States Patent
Wiesel (10) Patent No.: US 11,147,499 B2
(45) Date of Patent: Oct. 19, 2021

(54) METHOD AND APPARATUS FOR DETECTING ATRIAL FIBRILLATION

(71) Applicant: Joseph Wiesel, West Hempstead, NY (US)

(72) Inventor: Joseph Wiesel, West Hempstead, NY (US)

(*) Notice: Subject to any disclaimer, the term of this patent is extended or adjusted under 35 U.S.C. 154(b) by 194 days.

(21) Appl. No.: 16/284,188

(22) Filed: Feb. 25, 2019

(65) Prior Publication Data

US 2019/0298200 A1    Oct. 3, 2019

Related U.S. Application Data

(63) Continuation-in-part of application No. 15/595,858, filed on May 15, 2017, now abandoned, which is a
(Continued)

(51) Int. Cl.
*A61B 5/361* (2021.01)
*A61B 5/00* (2006.01)
(Continued)

(52) U.S. Cl.
CPC .............. *A61B 5/361* (2021.01); *A61B 5/024* (2013.01); *A61B 5/02416* (2013.01);
(Continued)

(58) Field of Classification Search
CPC ....... A61B 5/361; A61B 5/681; A61B 5/7207; A61B 5/024; A61B 5/02416; A61B 5/352;
(Continued)

(56) References Cited

U.S. PATENT DOCUMENTS

| 4,260,951 A | 4/1981 | Lewyn |
| 4,621,643 A | 11/1986 | New et al. |

(Continued)

FOREIGN PATENT DOCUMENTS

CN    205493806 U    8/2016

OTHER PUBLICATIONS

International Search Report received for PCT Application No. PCT/US2017/032768, dated Aug. 7, 2017, 2 pages.
(Continued)

*Primary Examiner* — Amanda K Hulbert
*Assistant Examiner* — Natasha Patel
(74) *Attorney, Agent, or Firm* — Bochner IP; Andrew D. Bochner (57) ABSTRACT

A method of determining atrial fibrillation includes determining if a patient's pulse beats form an irregular pattern. If so, presence of an irregular pulse is indicated to a patient and, an electrocardiogram is obtained for determining atrial fibrillation. Initially, a pulse is detected at regular time intervals from a first appendage when motionless, using a pulse detector and pulse rhythms from a succession of time intervals, each corresponding to a respective interval of time between successive pulse beats of a sequence of the pulse beats. Then, a second appendage makes contact with an electrically conductive unit, and electrocardiogram signals are detected simultaneously with pulse rhythms while the first appendage is motionless and both appendages are relaxed. The signals are then analyzed to determine whether, in combination, they are indicative of atrial fibrillation. If atrial fibrillation is determined not to be present based on analysis of said ECG, then the pulse analyzer is adjusted to not detect that pulse pattern as irregular.

20 Claims, 7 Drawing Sheets

Related U.S. Application Data continuation-in-part of application No. 14/469,023, filed on Aug. 26, 2014, now Pat. No. 9,681,819.

(60) Provisional application No. 61/871,906, filed on Aug. 30, 2013.

(51) Int. Cl.
  *A61B 5/024* (2006.01)
  *A61B 5/11* (2006.01)
  *A61B 5/352* (2021.01)

(52) U.S. Cl.
  CPC .......... *A61B 5/681* (2013.01); *A61B 5/7207* (2013.01); *A61B 5/02438* (2013.01); *A61B 5/11* (2013.01); *A61B 5/352* (2021.01); *A61B 5/6824* (2013.01); *A61B 5/721* (2013.01); *A61B 5/7214* (2013.01); *A61B 2562/0219* (2013.01)

(58) Field of Classification Search
  CPC ........ A61B 2562/0219; A61B 5/02438; A61B 5/11; A61B 5/721; A61B 5/7214; A61B 5/6824
  See application file for complete search history.

(56) References Cited

U.S. PATENT DOCUMENTS

| | | |
|---|---|---|
| 4,685,464 A | 8/1987 | Goldberger et al. |
| 4,700,708 A | 10/1987 | New et al. |
| 5,113,869 A | 5/1992 | Nappholz et al. |
| 5,117,834 A | 6/1992 | Kroll et al. |
| 5,228,449 A | 7/1993 | Christ et al. |
| 5,342,404 A | 8/1994 | Alt et al. |
| 5,456,261 A | 10/1995 | Luczyk |
| 5,471,991 A | 12/1995 | Shinnar |
| 5,588,425 A * | 12/1996 | Sackner ............... A61B 5/0245 600/513 |
| 5,609,158 A | 3/1997 | Chan |
| 5,626,143 A | 5/1997 | Meyer |
| 5,772,604 A | 6/1998 | Lang berg |
| 5,842,997 A | 12/1998 | Verrier et al. |
| 5,941,831 A | 8/1999 | Turcott |
| 6,095,984 A | 8/2000 | Amano et al. |
| 6,126,595 A | 10/2000 | Amano et al. |
| 6,249,700 B1 | 6/2001 | A lt |
| 6,327,499 B1 | 12/2001 | A lt |
| 6,519,490 B1 | 2/2003 | Wiesel |
| 7,020,514 B1 * | 3/2006 | Wiesel ................ A61B 5/361 600/518 |
| 7,072,709 B2 | 7/2006 | Xue |
| 7,680,532 B2 | 3/2010 | Wiesel |
| 7,706,868 B2 | 4/2010 | Wiesel |
| 9,215,998 B2 | 12/2015 | Reinhold, Jr. et al. |
| 2005/0113703 A1 | 5/2005 | Farringdon et al. |
| 2007/0276270 A1 | 11/2007 | Tran et al. |
| 2008/0103402 A1 | 5/2008 | Stickney et al. |
| 2008/0269626 A1 * | 10/2008 | Gallagher .......... A61B 5/02416 600/509 |
| 2010/0022897 A1 * | 1/2010 | Parker ................ A61B 5/02416 600/500 |
| 2010/0324384 A1 | 12/2010 | Moon et al. |
| 2012/0035435 A1 | 2/2012 | Choi et al. |
| 2012/0232416 A1 | 9/2012 | Gilham et al. |
| 2012/0265086 A1 | 10/2012 | Lux |
| 2013/0138002 A1 | 5/2013 | Weng et al. |
| 2015/0065891 A1 | 3/2015 | Wiesel |
| 2016/0287172 A1 | 10/2016 | Morris et al. |
| 2016/0338598 A1 | 11/2016 | Kegasawa |

OTHER PUBLICATIONS

Written Opinion received for PCT Application No. PCT/US2017/032768, dated Aug. 7, 2017, 6 pages.

Joseph Wiesel et al., "The Use of a Modified Sphygmonanometer to Detect Atrial Fibrillation in Outpatients," PACE, vol. 27 (May 2004), 6 pages.

Braunwald's, "A Textbook of Cardiovascular Medicine", 7th Edition, 2004, pp. 817, 840.

Degown's Diagnostic Examination, 8th Edition, 2004, p. 362.

* cited by examiner

METHOD AND APPARATUS FOR DETECTING ATRIAL FIBRILLATION

FIELD OF THE INVENTION

The present invention generally relates to a method of and an apparatus for detecting atrial fibrillation.

BACKGROUND OF THE INVENTION

The heart is a major muscle that functions as the primary pump for blood flow throughout the body. The heart contains two upper chambers called atria and two lower chambers called ventricles. The right atrium receives oxygen-depleted blood while the left atrium receives blood enriched with oxygen from the lungs. When the atria are full, the outlet valves within the heart open and the atria squeeze blood into the ventricles. The right ventricle then pumps oxygen-depleted blood to the lungs, while the left ventricle pumps oxygen-enriched blood to all parts of the body. In this fashion, the heart functions primarily as a double sided pump.

The heart's internal pacemaker, known as the sinus node, signals the start of each heartbeat. This signal originates in the right atrium in the sinoatrial node and travels simultaneously to the left atrium and down to the interatrial septum to the atrioventricular node. This electrical impulse results in a "p" wave on the electrocardiogram. This cycle of electrical stimulation that occurs normally is referred to as normal sinus rhythm. The contraction of the ventricles is preceded by QRS waves on the electrocardiogram (ECG), which is the electrical activity that begins ventricular contraction. This electrical activity is also often referred to as the "R" wave. The contraction of the heart occurs after the R wave. The impulse caused by cardiac contractility is transmitted through the arteries and is detected as a pulse. This pulse beat usually occurs from about 200 msec to about 700 msec after the R wave.

Many rhythm abnormalities may cause an irregular heart rhythm. Atrial fibrillation is a rhythm abnormality in which the atria do not contract normally. Instead, there is a continuously varying pattern of electrical activation of the atria resulting in a rapid highly irregular pattern of impulses reaching the atrioventricular node. The atrioventricular node acts as a filter and allows a reduced number of these impulses to reach the ventricles, which results in a highly irregular heartbeat pattern. Since there is no organized electrical activity in the atrium, atrial fibrillation does not produce a p wave on the ECG.

Atrial fibrillation is one of the most common arrhythmias requiring medical attention. Atrial fibrillation may be caused by a number of heart conditions, such as coronary artery disease, myocardial infarction, heart valve abnormalities, and high blood pressure. These conditions may stretch or scar the atria, thereby causing irregularities in the heart system. Atrial fibrillation may also accompany lung problems or thyroid gland disorders and is also associated with significant morbidity and possible mortality. All persons, young and old, female or male, including the visually and/or sight impaired, may experience atrial fibrillation.

The most serious complication of atrial fibrillation is formation of a blood clot in the left atrium, which may result in a stroke. The standard therapy used to prevent strokes in patients with risk factors for a stroke and atrial fibrillation is an anticoagulant, or blood thinner. Many people who develop atrial fibrillation, however, are unaware of their abnormal rhythm.

Recommendations have been made for people at risk of developing atrial fibrillation to check their pulse periodically. Checking the pulse manually by palpation is often difficult for some people, especially the elderly, to do reliably. Therefore, use of a device that periodically automatically assesses the heart rhythm and alerts the patient to the presence of atrial fibrillation would be helpful in getting patients with atrial fibrillation to be treated earlier. This may help prevent strokes in patients who are unaware that they have atrial fibrillation.

There are devices available that can be used by patients to screen for atrial fibrillation. The electrocardiogram (ECG) is the gold standard for determining if a person has atrial fibrillation. However, checking the ECG is cumbersome because it requires the person to place at least two electrodes on different body locations, such as both arms, an arm and a leg or an arm and the chest, or two locations on the chest. Also, ECG monitoring at home often requires a technician, and then a physician to read the ECG. The cost of this approach is prohibitive for the general population at risk of atrial fibrillation.

There are devices that can read the ECG automatically. However, they are easily compromised by a noisy signal, which is very common with ECG's. A noisy ECG signal can result in what is described as "artifacts" on the ECG signal. These artifacts can appear to be multiple R waves in an irregular pattern. These artifactual R waves will not have p waves preceding them and will, thus, result in the ECG meeting the criteria for diagnosing atrial fibrillation even though the true rhythm may be regular.

The use of blood pressure monitors and smartphones which can determine the time interval between pulse beats have been described. The blood pressure monitors rely on plethysmographic signals to detect the pulse, while smartphones can use the light transmittance through the skin to detect the pulse. The blood pressure devices, in particular, are able to detect the pulse reliably with artifacts rarely affecting the pulse signal. These modalities rely on assessing the regularity of the pulse rhythm, which is irregular in atrial fibrillation. However, other rhythm abnormalities, such as extra heart beats, may cause an irregular heart rhythm. These extra beats often follow normal beats that have both p and R waves on the ECG. Differentiating the rhythms due to extra heartbeats from atrial fibrillation can therefore be performed most accurately by using the ECG.

Combining both the ECG recording and the pulse recording can improve the accuracy of detecting the true pulse beats. As mentioned previously, noise in either the ECG or pulse rhythm recording can result in artifacts that look like extra beats. Heart beats that occur with an adequate time interval following the previous beat to generate a pulse will always generate an R wave on the ECG and a pulse beat. Therefore, it is possible to use the pulse rhythm recording to help determine if what looks like an R wave on the ECG is due to a very premature R wave or an artifact, since that electrical activity will not have a pulse beat. By deleting that electrical activity from the ECG, it is possible to generate a modified ECG that will have less electrical noise and a reduced number of very premature beats. This new modified ECG recording can then be analyzed for regularity. If it is regular, then the rhythm is not atrial fibrillation. If it is irregular, then the R waves on the modified ECG can be identified, and an attempt can be made to detect the preceding p waves. If the p waves are present, then the rhythm is not atrial fibrillation. If the p waves are absent, then the rhythm is atrial fibrillation.

The ECG recording and the pulse rhythm recording can be most easily compared by shifting the time of the ECG by from about 200 msec to about 700 msec so that the R waves occur at a later time. When the ECG time is shifted enough to account for the delay in generating the pulse rhythm, then the ECG and pulse recordings should have R waves and pulse beats occurring simultaneously. That is the time shift that can be used to generate the new modified ECG recording.

Using the pulse to screen for atrial fibrillation is very convenient because it can be done automatically if the pulse detector is mounted on a wearable device. However, the pulse detector is subject to false positive readings due to frequent premature beats. The pulse detector may detect an irregular rhythm that is then determined by use of the ECG not to be atrial fibrillation. In that case, it would be useful to be able to modify the pulse detector analyzer so as to not detect this particular rhythm as irregular in the future. This would reduce the number of false positive determinations, thereby, reducing the number of times that the individual would need to manually take an ECG reading. Without this feature, those with frequent premature beats may choose not to use this device due to frequent false positive readings.

Attempts have been made to utilize a wristwatch for acquiring an ECG signal, but such systems have been cumbersome and inaccurate. Previous methods required an individual to place one finger from the non-watch hand onto an electrode. This electrode was then placed on the outside face of the watch, with a second electrode attached to the inside surface of the watch. The second electrode was in contact with the skin of the wrist on which the watch is worn.

In another attempt to utilize a wristwatch for ECG recording, an individual would place a thumb from the non-watch hand on an electrode located on the outside surface of the watchband. A second electrode would be located on the inside surface of the watchband, and would be in contact with the skin of the wrist on which the watch is worn.

However, these attempts to utilize a wristwatch in these manners would result in noise generated by contraction of the muscles in the arm and hand. In addition, small movements of the finger in contact with the electrode, which can develop due to fatigue from actively pressing on the electrode, can result in a noisy signal.

Previous methods, such as those described in the Righter patent (U.S. Pat. No. 5,226,425), provide for recording an ECG automatically only when both ECG electrodes came into contact with a person's skin. As a result, battery life is prolonged by only recording when both electrodes are in position to record a signal. Less memory is required for storing the ECG signal by recording only when both electrodes contact skin. The Righter method is effective for use in an ECG when one electrode is in continuous contact with the skin, such as under the watch, but the second electrode is only in selective contact with the skin, such as being on the outer surface of the watch, where it is in contact with skin on the opposite hand only when a hand is placed over it to record an ECG. However, Righter's method is not effective, and unusable, when there is continuous contact of both electrodes with the skin.

Methods for determining if an ECG waveform is noisy have been described in U.S. Pat. No. 8,639,316. However, the presence of noise is determined by analyzing the properties of the ECG signal such as the morphology, amplitude or frequency content of the signal. This can also be applied to other physiological signals such as blood pressure waveforms. Yet, there is no mention of using a combination of physiological signals to determine if the ECG signal is noisy. There is also no mention of generating a new ECG recording by using a physiological signal to modify the ECG signal and then using that modified ECG to determine if atrial fibrillation is present.

U.S. Pat. Appln. Publ. No. 20130060154 describes a watch-like device that is worn on the wrist and can detect pulse signals which can be used to determine if atrial fibrillation is present. However, it does not describe obtaining recordings periodically and automatically when the person is not moving.

It would be desirable, therefore, to provide an alternative method of activating and turning on ECG recording.

It would be further desirable, therefore, to provide a device that can be worn on a daily basis and can periodically take automatic pulse readings when a person is not moving so, as to accurately determine if the heart rhythm is irregular.

It would be further desirable to provide a device that accurately measures ECG signals, without the need for actively pressing on an electrode.

It would be yet further desirable to provide a method for recording an ECG while allowing for a patient's arm to be in a relaxed position.

It would be yet further desirable to provide a device and method to inform a patient when the automatic pulse reading showed an irregular rhythm and a combined ECG and pulse rhythm recording needs to be taken.

It would be yet further desirable that the pulse beat analyzer is able to modify the algorithm for determining when an irregular pulse may be atrial fibrillation based on the determination that a previously detected irregular pattern was not atrial fibrillation.

It would be yet further desirable to provide a device and method for combined pulse and ECG recording to be analyzed, in order to determine if atrial fibrillation is present.

It would be yet further desirable to provide a device and method in the form of a watch or wrist accessory, in which one electrode is in constant contact with the wrist of the patient on which it is placed, and automatically turns on the ECG recording only when the fingers of the non-watch hand come in contact with the second ECG electrode.

SUMMARY OF THE INVENTION

Methods and devices for improving electrocardiogram (ECG) recording using a wristwatch are provided. The wristwatch may reside on a first arm. The first arm may include a first hand. The methods and devices may include a wristwatch with a first electrode on its undersurface. The first electrode may be in contact with the skin of the wrist upon which it is worn.

The methods and devices may include a second electrode on the inside surface of a watchband in connection with the wristwatch. The second electrode may be located approximately 180 degrees relative to the location of the first electrode, along a circular path formed by the wristwatch and the watchband.

The methods and devices may include recording an ECG when one or more fingers from a second hand associated with a second arm (i.e. the one not wearing the wristwatch), are placed on the inside surface of the watchband, between the watchband and the wrist. The ECG may, in one embodiment, only be recorded when the one or more fingers from the second hand are placed between the watchband and the wrist, and come into contact with the second electrode on the inside surface of the watchband.

The methods and devices may further include recording the ECG when both arms and hands are in a relaxed positon. The methods and devices may yet further include recording the ECG only when both arms and hands remain in continued contact with both electrodes.

In an embodiment, the methods and devices may further include recording the ECG only when tension of the watch and watchband on the wrist of the first arm is provided by the fingers of the second arm, such that continuous contact with both electrodes is provided.

Other features and advantages of the present invention will become apparent from the following detailed description of the invention with reference to the accompanying drawings.

BRIEF DESCRIPTION OF THE DRAWINGS

For a better understanding of the present invention, reference is made to the following description and accompanying drawings, while the scope of the invention is set forth in the appended claims:

DETAILED DESCRIPTION OF THE INVENTION

An apparatus and method for activating and switching on and off an ECG recording is provided. The apparatus and/or method may be worn or utilized on a daily basis, and may periodically record automatic pulse readings when a person is not moving to determine the presence of atrial fibrillation.

In an embodiment, the apparatus and method are configured for receiving a finger, or plurality of fingers, under a watchband, reducing the likelihood that the finger will move. In accordance with this embodiment, holding the finger fixed to the watchband is easier than holding the finger fixed to the housing, allowing for the finger to passively rest on the inside of the watchband in contact with the electrode.

The apparatus/method includes features to accurately measure ECG signals, without the need for actively pressing on an electrode associated with the ECG. The ECG may be recorded while a patient's arm is in a relaxed position.

In an embodiment, a patient may be informed when the automatic pulse reading displays an irregular rhythm, and a combined ECG and pulse rhythm recording needs to be taken.

In an embodiment, a wristwatch or wrist accessory may be used to record the ECG, in which one electrode is in constant contact with the wrist of the patient on which it is placed, and automatically turns on the ECG recording only when the fingers of the non-watch hand come in contact with the second ECG electrode.

In an embodiment, a device that takes a pulse reading using light transmittance through the skin could automatically determine if the pulse is irregular and the individual may be in atrial fibrillation. If the rhythm is irregular then an ECG can be recorded simultaneously with the pulse recording in order to verify if atrial fibrillation is present. This can be accomplished with a wristwatch based device.

A device that uses the pulse beats as the first step in determining the presence of atrial fibrillation may detect other irregular rhythms as atrial fibrillation. This could result in frequent false atrial fibrillation alarms. Therefore, the algorithm that determines that a pulse rhythm may be atrial fibrillation should be automatically modified if it is determined that a particular rhythm is not atrial fibrillation. In other words, the algorithm should be able to learn from its mistakes how to better identify atrial fibrillation in a particular individual. That modification may be based on analysis of the combined ECG and pulse rhythms.

In an embodiment, the devices and methods screen for atrial fibrillation periodically by automatically checking for a pulse irregularity when the appendage, on which the apparatus is worn or secured, is motionless. It then adds an additional step to determine if atrial fibrillation is present when the pulse rhythm is found to be irregular, by taking a combined ECG and pulse reading. In this combined reading, the presence of atrial fibrillation may be determined by (i) detecting the pulse beat intervals and the ECG signal simultaneously when at least one appendage is motionless, (ii) generating a new modified ECG recording that includes only heartbeats that are present on both the ECG and pulse rhythm recording, (iii) analyzing the modified ECG recording for regularity or irregularity, (iv) if an irregularity is found, then determining if "p" waves are present preceding the R waves on the modified ECG, (v) determining if atrial fibrillation is present by the lack of p waves, and (vi) communicating this information to the user so that a medical practitioner may be consulted by the user for further testing and/or treatment.

In accordance with an embodiment, the quality of an ECG signal may be improved by reducing noise generated by skeletal muscle activity, such as muscle activity in the arms or other areas. Noise is reduced by maintaining contact between the individual's skin and ECG electrodes. In an embodiment, a plurality of electrodes, such as two electrodes, may be placed on an interior surface of a wristwatch device used to detect ECG signals. In another embodiment, the two electrodes may be placed on wristwatch and watchband (one on each). In yet another embodiment, two electrodes may be placed on the watchband. Each electrode may be used by one of each of the individual's aims and hands, such that at least one finger from the non-watch hand is placed on one electrode, and the wrist from the watch-wearing hand is in contact with the other electrode.

The device and method may compensate for loss of signal amplitude resulting from one electrode contacting both arms. That is, the electrode receiving the signal from the non-band watchband-wearing hand may also make contact with skin of the wrist of which the watchband is worn thus getting an electrical signal from both arms simultaneously. This reduces the amplitude of the ECG signal detected by the device. However, in accordance with an embodiment where contact with the electrodes is maintained without any muscular activity, the noise level is reduced even more than the ECG signal amplitude is reduced. As a result, the signal to noise ratio is increased and the diagnostic quality of the electrical signal improves. Therefore, in accordance with this embodiment, a method and device is provided that does not require active pressing on an electrode.

In another embodiment multiple small electrodes are place on the interior surface of the wristwatch device and band. The skin of the wrist upon which the watchband is worn will make contact with multiple electrodes and the finger or fingers of the non-watch hand will make contact with one or more electrodes. The ECG processor can analyze the signal from each pair of electrodes and select the pair of electrodes that provide the best ECG signal for recording. The best ECG signal being the ECG signal with the largest amplitude and the least noise. This embodiment avoids the situation where one of the electrodes used to record the ECG signal is in contact with the skin of both arms simultaneously as described in paragraph 53.

In an embodiment, the amount of noise in the ECG signal obtained from the arms may be reduced if both arms could be relaxed and the ECG electrodes are allowed to make firm contact with the skin passively. This can be accomplished by having elastic conductive wrist bands placed tightly on each wrist, and then relaxing both arms. Though one wrist band may be a watch band worn continuously, placing the second wrist band on the other hand would be cumbersome.

In an embodiment, placing the two electrodes for both arms on the inside of one wrist band may address the issue. When an ECG needs to be recorded, the fingers from the non-wristband hand arm may be slipped underneath the band, stretching the band and contacting the second electrode, while the first electrode remains in contact with the skin of the wrist on which the band is worn. By stretching the band with the fingers, firm contact of the skin with both electrodes is assured. In addition, the tension on the band would keep the fingers from moving even if the hand is completely relaxed. Thus, slipping the fingers under the wrist band, contacting the second electrode, and then allowing both arms to fully relax would reduce the noise in the ECG signal. Though the second electrode may be in contact with the fingers of the non-wristband hand, it may, on occasion, also be partially in contact with the skin of the wrist upon which the band is worn. Though contacting both aims simultaneously with one electrode will reduce the ECG amplitude, the greater reduction in noise achieved by this technique results in a higher signal to noise ratio, improving the ability to analyze the ECG signal for atrial fibrillation.

In an embodiment, a method of and an apparatus for detecting irregular pulses and ECG rhythms during a time period and storing this information for comparison with the pulse rhythm at later time periods is provided. The present invention may also detect patterns over multiple time periods and compare the patterns over various time periods.

Pulse beats may be obtained by plethysmography such as the use of an inflatable cuff wrapped around a person's appendage, such as a wrist, which detects the pulse beats by either oscillometric or auscultatory means. The time intervals between pulse beats can be determined during cuff deflation or while the cuff is inflated at a fixed pressure. This cuff device can be incorporated into a wrist watch that can be worn on a daily basis and automatic recordings obtained periodically, such as once a day or once a week. The device would inflate the cuff only when the wrist has been stationary and motionless for a specified time period before the inflation as determined by an accelerometer within the device. The waveform generated by the device would only be analyzed if the accelerometer confirmed that no movement occurred during the measurement period.

Pulse beats may also be monitored through changes in light transmitted through various body appendages. Each pulse beat changes the light transmission through a location on the appendage. The change in the light transmission corresponds to a pulse beat and the time intervals between pulse beats may be determined. This can be done with a wrist watch device that includes a light source and a light sensor on the part of the wrist watch that makes contact with the skin at the wrist. This wrist watch that can be worn on a daily basis and automatic recordings can be obtained periodically, such as once a day or once a week. The device measures light transmittance only when the wrist has been stationary and motionless for a specified time period before the measurement as determined by an accelerometer within the device. The waveform generated by the device would only be analyzed if the accelerometer confirmed that no movement occurred during the measurement period.

Pulse beats may also be monitored using other plethysmographic devices, ultrasound devices that measure arterial motion with each pulse beat, ultrasound doppler devices that detect blood flow within an artery or devices that rely on localized compression of the artery to detect the presence of a pulse beat. Using any of these techniques the time intervals between pulse beats can be determined.

ECG signals may be obtained by placing electrical conducting leads on the limbs, other appendages or the chest. It may also be obtained by obtaining electrical signals from conducting leads in the heart or in other locations in the chest such as in pacemakers.

A monitoring method of the present invention includes communicating this information to a user such as via a screen display, a paper printout, a tone, or auditory, vibratory or other sensory communication.

The invention may utilize algorithmic or heuristic techniques to determine whether the ECG and pulse beats signal the possible presence of atrial fibrillation.

Figure 1:
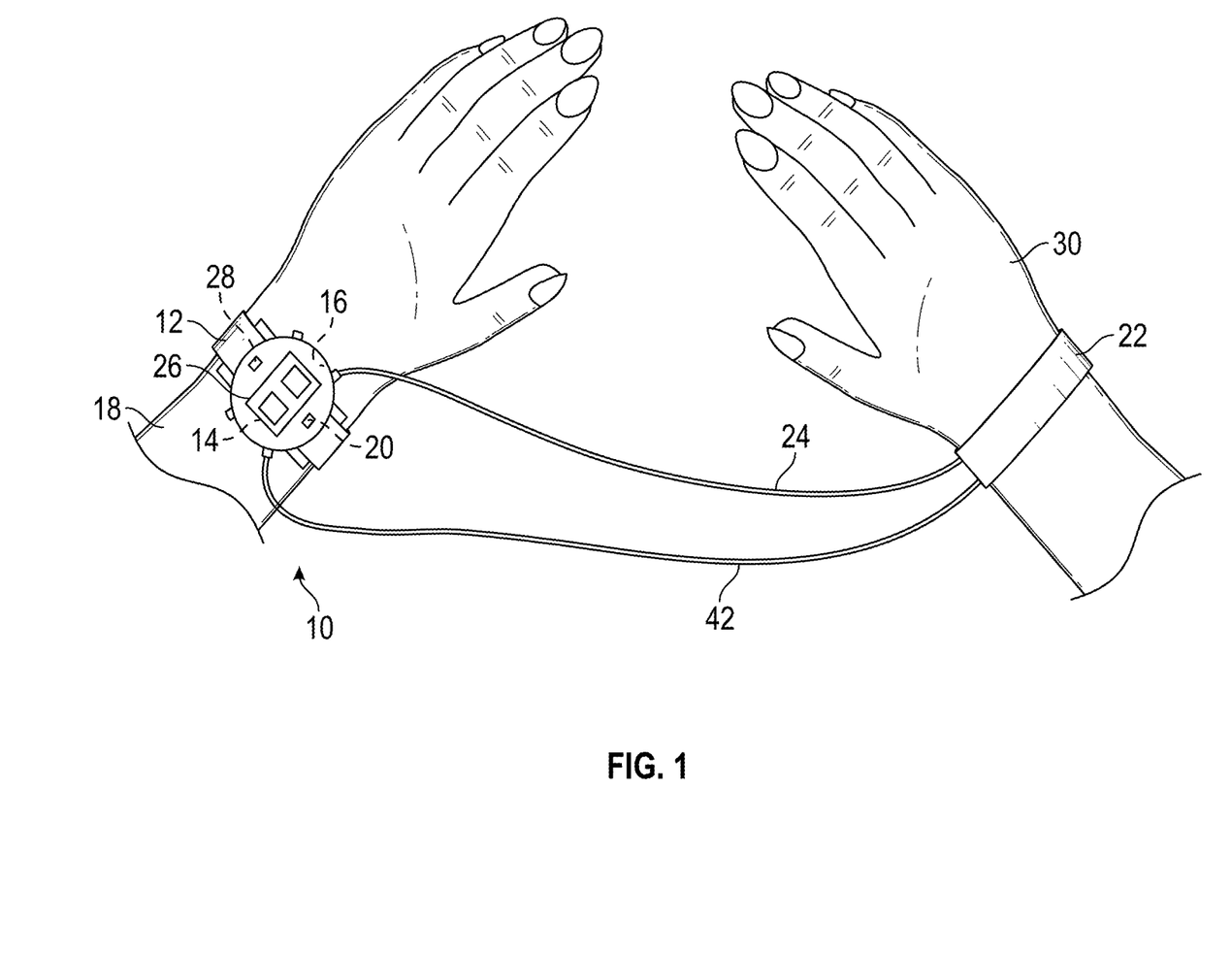
FIG. 1 is shows an exemplifying, non-limiting embodiment of a wrist watch in accordance with the invention.

Referring to the accompanying drawings wherein like reference numbers refer to the same or similar elements, one embodiment of the apparatus in accordance with the invention and that may be used in a method in accordance with the invention uses pulse beats and an ECG that are detected using a wristwatch 10 which has a conductive watch band or strap 12 as shown in FIG. 1. The watch band or strap 12 is an example of a securing mechanism for securing a housing 40 including the electrical and mechanical components of the invention to the wrist of the patient. Other securing mechanisms may be used in the invention.

The wrist watch 10 also includes a light source 14 and sensor 16 on the bottom side of watch 10, preferably directly on or against the skin surface 18. The light source 14 and light sensor 16 are controlled to transmit light to the skin of the wearer and receive reflected light which can be converted into a pulse in a manner known to those skilled in the art to which this invention pertains. Other pulse detector mechanisms may also be used in the invention and included in the housing of the watch 10 that is secured to the wrist of the wearer, or another appendage of the wearer.

An accelerometer 20 is preferably built into the housing 40 of the watch 10. The ECG is obtained from electrically conductive portions in wrist straps 12, 22 on and in skin contact with both wrists of the same person with a limb lead 24 from strap 22 connected to the housing 40 of the watch 10. Data from the accelerometer 20 is used to determine whether the wrist to which the watch 10 is secured is sufficiently motionless or moving. In this context, motionless means that the position of the wrist is not changing. A totally still state of the appendage is desirable but practically difficult to achieve. Therefore, a threshold may be set as to the degree of permissible motion of the appendage and an indication of motion below the threshold may be considered a motionless state.

Since the light source 14 and sensor 16 are operative on the underside of the watch 10, and hence in dotted lines in FIG. 1, the wrist watch 10 would be able to keep track of time via a conventional time keeping and displaying mechanism 26 visible to the wearer and determine when the next automated pulse reading should be obtained. A timing mechanism to achieve this timed determination is readily configured to one skilled in the art in view of the disclosure herein. For example, pulse readings may be obtained once a day to detect if the patient has an episode of atrial fibrillation. The wrist watch 10 would automatically begin to determine if the wrist is moving when the time for the next pulse reading occurs. This movement detection is preferably performed using the accelerometer 20, but as an alternative, another movement detection means or mechanism may be used in the invention.

If the accelerometer 20 determines that the wrist is moving at that time, it will not attempt to take a pulse reading. The accelerometer 20 may be used to check for movement again a set period of time later, e.g., five minutes later, and continue to enable such movement checking until it is found that the wrist is motionless. At that time, a 30 second pulse rhythm will be obtained. If data from the accelerometer 20 confirms that no movement occurred during that 30 second reading, then the pulse rhythm obtained during the 30 second period will be analyzed to determine if the pulse rhythm is regular or irregular. If it is regular, then atrial fibrillation is not present and the watch 10 will obtain the next reading according to its programmed schedule, e.g., the following day at the same set time.

If the pulse rhythm is irregular, the watch 10 will signal the person wearing the watch 10 by voice, beeping, vibration, a text, a light or on the watch screen display 26, that an abnormal rhythm was found and an ECG needs to be taken. The mechanism that provides this is referred to as a signaling mechanism 28 and may be incorporated into the housing 40 of the watch 10. The signaling mechanism 28 may be configured to perform one or more of these actions or responses to the determination of the irregularity of the pulse rhythm by the processor 32 in the housing 40 of the watch 10 (see FIG. 2).

Once notified that an ECG needs to be taken, the person should then take a conductive wrist strap 22 that is incorporated in the wristwatch band 12 and pull it off the watch band 12 and place it on the other wrist (as shown in FIG. 1). The wrist strap 22 will have a wire or lead 24 that is in place connecting it to the housing of the watch 10, i.e., to the electronic componentry in the housing of the watch 10 (schematically shown in FIG. 2). A connector 42, e.g., an elastic cord, is optionally provided to connect the wrist strap 40 to the housing 40. Once the second wrist strap 22 is in place, the conductive wristwatch band 12 and the other wrist strap 22 become two leads for the ECG. The wristwatch band 12 is positioned to have continuous contact with the skin surface 20 on the wrist and the watch 10, i.e., processor 32 therein, can detect that the second wrist strap 22 has made contact with the skin surface 30 since an ECG signal will then be generated.

At that point, data from the accelerometer 20 will be used to determine if the wrist watch 10 is motionless. If it is not, then the wrist watch 10 will signal to the person to stop moving both arms and to relax. If data from the accelerometer 20 provides a determination that there is no movement, then the ECG and the pulse rhythm will be recorded simultaneously for 30 seconds. This recording may be stored in a memory 34 of the housing of the watch 10 (see FIG. 2).

Figure 2:
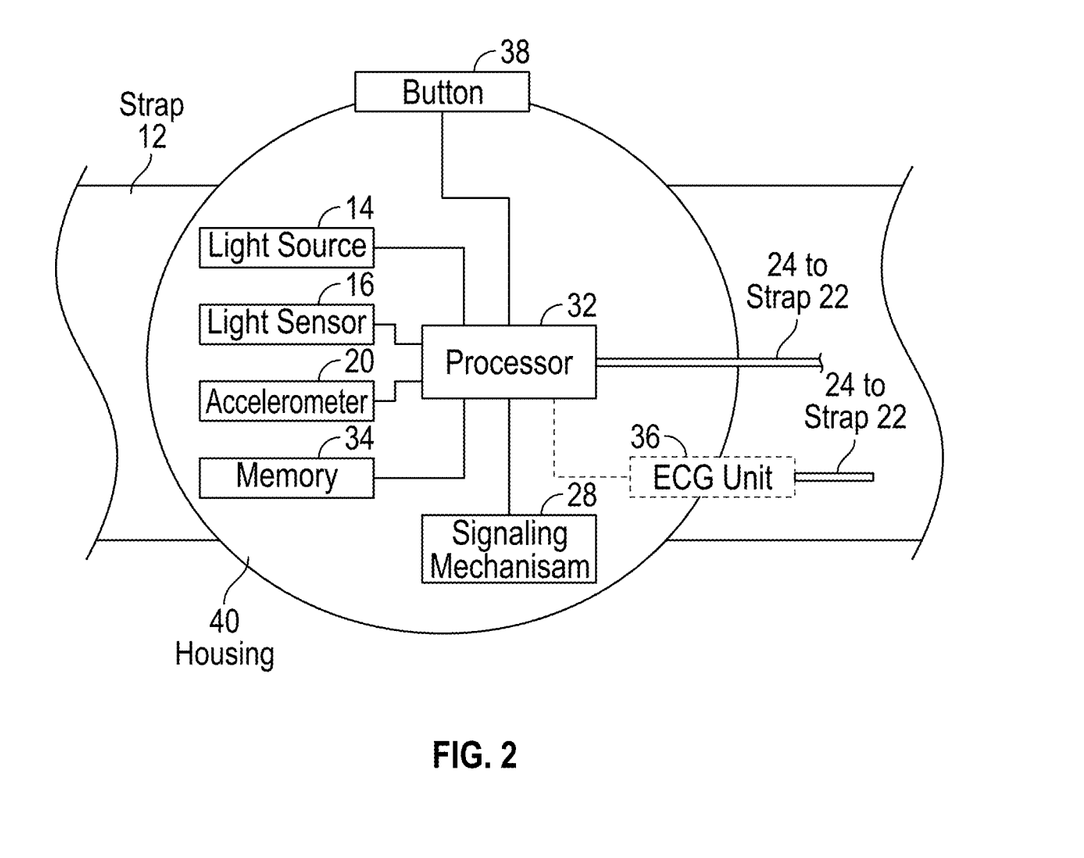
FIG. 2 is a schematic showing the components in the housing of the wrist watch in accordance with the invention.

Once the ECG and pulse signals are obtained, the processor 32 in the wristwatch 10 will analyze the two signals (see FIG. 2). The pulse rhythm recording will be used to help the processor 32 determine if what looks like an R wave on the ECG is due to a very premature R wave or an artifact. Electrical activity on the ECG that does not have a pulse beat associated with it will be deleted (through processing performed by the processor 32 upon execution of appropriate software being executed by the processor 32). By deleting that electrical activity from the ECG, the processor 32 is configured to generate a modified ECG that will have less electrical noise and very premature beats.

This new modified ECG recording can then be analyzed by the processor 32 for regularity using algorithms or other processing techniques. If it is regular, then the rhythm is not atrial fibrillation and the person will be informed by voice, by a green light or by the watch screen that the rhythm is normal, via the signaling mechanism 28, and the next automatic reading will be performed as scheduled. If it is irregular, then the R waves on the modified ECG can be identified by the processor 32, and an attempt can be made to detect the preceding p waves. If the p waves are present, then the rhythm is not atrial fibrillation and the person will be informed that the rhythm is normal, again by means of the signaling mechanism 28. If the p waves are absent, then the rhythm is atrial fibrillation and the person will be informed that he has atrial fibrillation via the signaling mechanism 28 and should seek the advice of a physician. After the person acknowledges that he has received this message by pressing a button 38 on the watch 10, then the watch 10 will take the next reading as scheduled. If no acknowledgement is made, then the watch 10 will continue to show that atrial fibrillation was detected.

The processor 32 can store the time of each pulse beat, the intervals between pulse beats and other information in the memory 34 (see FIG. 2). The memory 34 may include RAM or other device memory or include a hard disc, a floppy disk or other memory devices. The processor 32 may comprise a microprocessor, and applications specific integrated circuit (ASIC), a programmable logic array (FLA) or reduced instruction set chip (RISC).

Instead of incorporating the ECG determination and analysis unit in the processor 32, the ECG device may be a separate ECG recorder with a signal output that can be connected to the wrist watch processor 32 (see ECG device 36 in dotted lines in FIG. 2). The wrist watch 10 may also have one lead incorporated into other accessories on the device such that it can be strapped onto the limbs or chest of the patient. The ECG device 36 may thus be a wearable electrocardiogram device configured to be attached to the limbs or the chest of the patient and provides an electrocardiogram signal to the processor 32 via an electrical lead (in dotted lines in FIG. 2).

Figure 5:
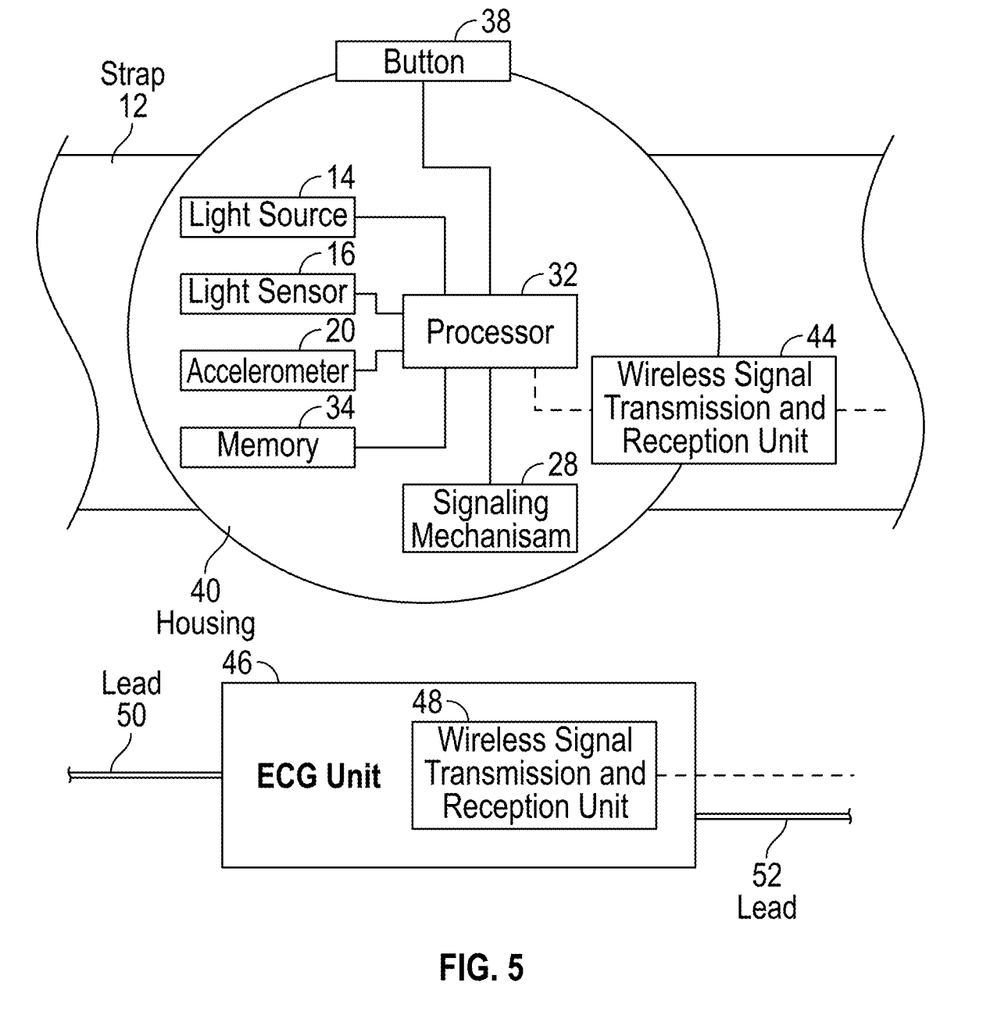
FIG. 5 is a schematic similar to FIG. 2 but including a wireless ECG device.

Referring now to FIG. 5, the wrist watch 10 may also communicate wirelessly with a separate ECG device 46 that may have leads 50, 52 placed upon the person's limbs or chest or is worn by the person. The wireless communication may be with radio waves using Bluetooth, near field communication technology or other data communication technologies. One embodiment using wireless technology would include the ECG device 46 that is separate and apart from the housing 40 of the wrist watch 10, and which would incorporate a wireless signal transmission and/or reception unit 48, and two or more electrically conductive leads 50, 52 that are adapted to be secured or otherwise attached at a respective location to the person for which the ECG is to be taken, specifically in contact with skin of the person. The ECG device 46 may thus be configured as a wearable electrocardiogram device attachable to the limbs or chest of the patient with the leads 50, 52 extending therefrom to be positioned in contact with skin of the patient. The housing 40 of the wrist watch 10 is then also provided with a wireless signal transmission and/or reception unit 44 and configured to issue commands to be wirelessly transmitted to the ECG device 46 to cause the ECG device 46 to obtain an electrocardiogram signal via the leads 50, 52 and output an ECG which is then transmitted to the wrist watch 10 via the wireless signal transmission and/or reception units 44, 48. An example of a wearable electrocardiogram device 36 that may be used in the invention is a T-shirt manufactured by HealthWatch of Tel Aviv, Israel.

In either case, the processor 32 deter nines from the pulse beats and ECG if the results suggest atrial fibrillation or not. Programming of the processor 32 to perform this determination is readily ascertainable by those skilled in the art in view of the disclosure herein. The processor 32 can then deliver the results to a printer, a display, a vibration generator, and/or an auditory generator, etc. (signaling mechanism 28) which may include an indication that the pulse beat pattern is regular, irregular, in possible atrial fibrillation, or that a physician should be contacted. Other information, such as the pulse rate, may also be displayed.

Figure 3:
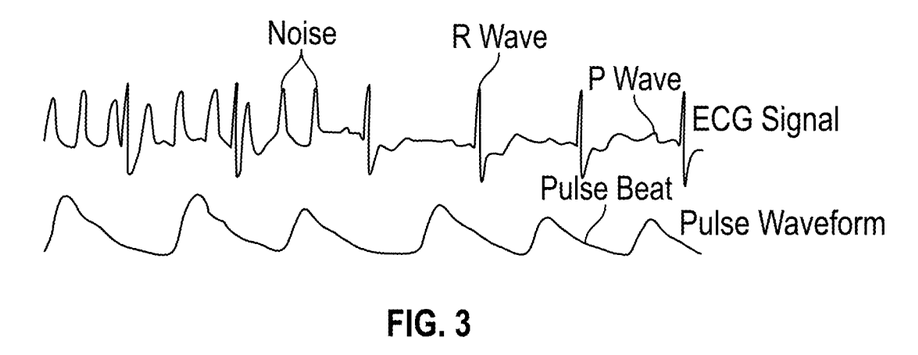
FIG. 3 is an example of an ECG signal with noise and a simultaneous pulse beat waveform obtained from a pulse oxymeter.

FIG. 3 shows an exemplifying ECG signal, the top signal, simultaneous with a pulse waveform, the bottom signal. The diagonal lines extending between the ECG signal and the pulse waveform show the R wave with the resulting pulse beat generated by the cardiac contraction caused by the R wave. ECG waveforms that do not have a resulting pulse beat are due to electrical noise. The noise stops after the third R wave. In this example of a recording, the ECG signal shows noise artifact that cannot easily be differentiated from the real R waves.

Figure 4:
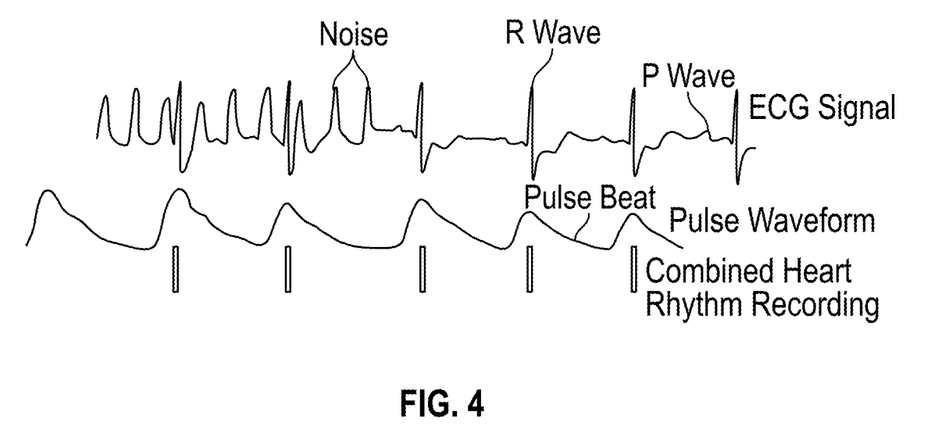
FIG. 4 shows the ECG time shifted so that the R waves coincide with the pulse beats and location of the R waves that would not be deleted from the new modified ECG.

FIG. 4 shows an exemplifying ECG signal, the top signal, time shifted so that pulse beats, the middle signal, coincide with R waves. The noise artifact on the ECG signal can then be ignored since they do not coincide with the pulse beats. Combined heart rhythm recording, the lower signal, shows which wave would not be deleted from the new modified ECG generated by the processor 32 in the manner described above, i.e., the new ECG recording can be generated at each time point where both R wave and pulse beats occur simultaneously. If this heart rhythm recording were regular, then the rhythm would be determined not to be atrial fibrillation. However, since this heart rhythm recording is irregular, further analysis of the modified ECG is needed to determine the presence or absence of p waves. The R waves are analyzed by the processor 32 to determine if there are p waves that preceded them. Since p waves are noted before the R waves on this tracing, the rhythm would be called not atrial fibrillation.

Figure 6:
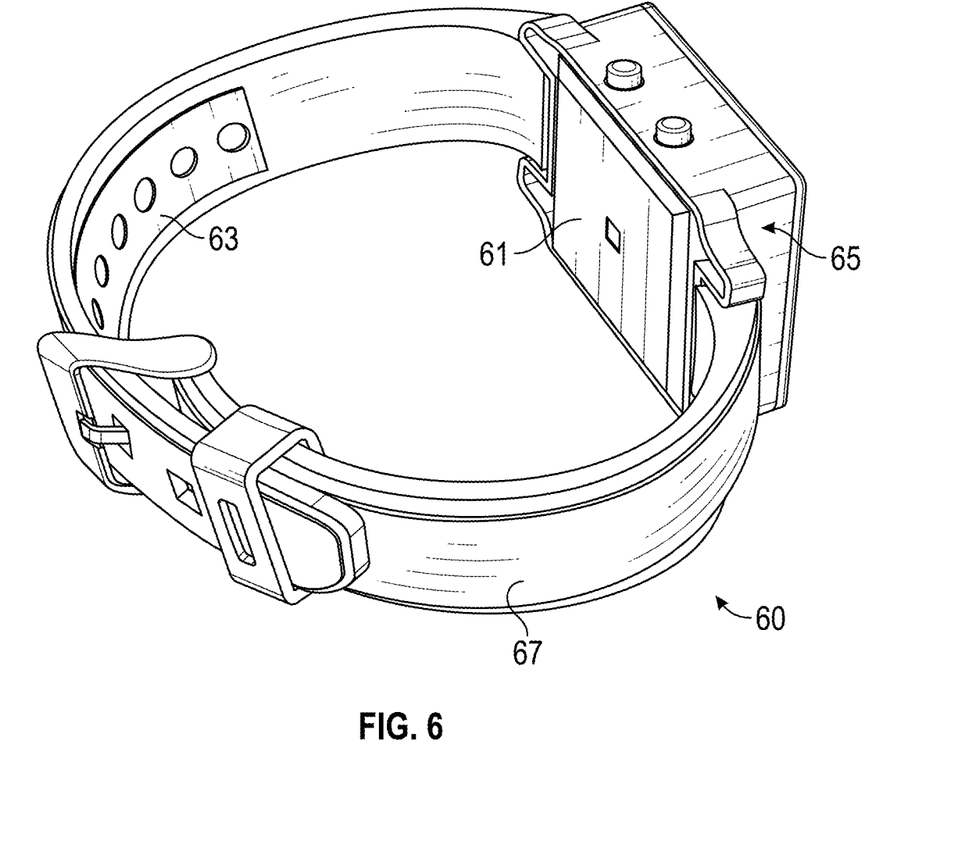
FIG. 6 illustrates an embodiment of the wristwatch with exemplary locations of both electrodes.

FIG. 6 illustrates an exemplary device and method in accordance with another embodiment. As shown, the patient/wearer is able to utilize the device while allowing the arm muscles to remain in a relaxed position. Thus, the arm muscles are able to remain relaxed, and the patient can remain in a sitting position. In accordance with this embodiment, the patient need not lie in a prone position to relax the thorax muscles, and instead may remain seated, with the arms completely relaxed.

In the embodiment of FIG. 6, a wrist watch 60 may incorporate some or all of the features of wrist watch 10, as well as any or all of the features previously described herein. Additionally, some or all of the components of wrist watch 60 may include some or all of the features of the components previously described.

The wrist watch 60 includes an ECG electrode 61 and ECG electrode 63. ECG electrode 61 is located on an underside of the watch housing 65, and is therefore always in contact with the wrist of a patient. ECG electrode 63, a second electrode, is located at a second location. The second location may include, but is not limited to, an internal surface of the band 67 of the watch, such as shown in FIG. 6, an outer surface of the watch band, or a removable portion of the watch.

In accordance with this embodiment, the presence of both ECG electrode 61 and ECG electrode 63 on the interior skin-contacting portion of the watchband 67 may result in a reduction in the amplitude of the ECG signal if one electrode comes in contact with both the watchband wearing arm and the fingers of the opposite hand.

However, in this embodiment, the configuration as shown in FIG. 6 does not cause the absolute noise level to increase, and instead causes a reduction of noise level when recording the ECG that more than offsets the loss of signal amplitude.

As illustrated, therefore, electrodes 61 and 63 are placed on the interior side of the watch 60 and watchband 67, respectively. In another embodiment, either or both of electrodes 61 and 63 may be placed on the interior of watchband 67.

For example, wristwatch 60 may be worn on a patient's right hand. ECG electrode 61, located on the underside of housing 65, is in continuous contact with the patient's right wrist. ECG electrode 63, located on the underside of watchband 67, is also in contact with the right wrist. In accordance with this embodiment, the wristwatch 60's ECG recording is switched off, until the patient inserts two fingers from the left hand under the watchband 67. Thus, the two fingers from the left hand come into contact with ECG electrode 63. In a further example, at this time, when the two fingers from the left hand are in contact with ECG electrode 63, the ECG recording is switched on, allowing for recording of the ECG when the patient is an upright position, with the arms fully relaxed.

In accordance with this embodiment, at least one electrode, such as electrode 61, remains in constant contact with the wrist of a patient when worn. Upon receiving a signal or indicator to activate the ECG recording, only then does the device begin recording ECG activity.

Thus, ECG recording is only activate when fingers of the non-watch hand, contact the second electrode 63. Indication of contact may include the sensor configured to determine the presence of one or two fingers. In another embodiment, a switch may be activated when the two fingers are present on the second electrode 63, and only then may recording of the ECG commence. In yet another embodiment, the watchband 67 includes a sensor that determines that the band is stretched, such that two fingers are placed below it.

In an embodiment, the watchband 67 may be stretchable. Thus, the lugs of the watchband 67 may be stretched. In another embodiment, the watchband 67 may not be stretchable. The watchband 67 is able to receive one or more fingers, such as two or three fingers, between the watchband 67 and the wrist upon which it is worn. In one embodiment, the stretching of the watchband 67, or the stretching of the lugs, activates the ECG recording. In another embodiment, the location of one or more fingers under the watchband causes a sensor to sense the presence, and activate recording of the ECG. In yet another embodiment, the patient may activate a switch, such as on the side of the housing 65, or on the watchband 67 itself, to activate ECG recording.

Once the fingers from the opposing hand are placed under the watchband 67, between the watchband and the wrist, sufficient tension is formed so as to support the wrist and fingers when both are in the relaxed state, while still ensuring contact of both electrode 61 and electrode 63 with the skin of the wrist and the fingers, respectively.

Figure 7:
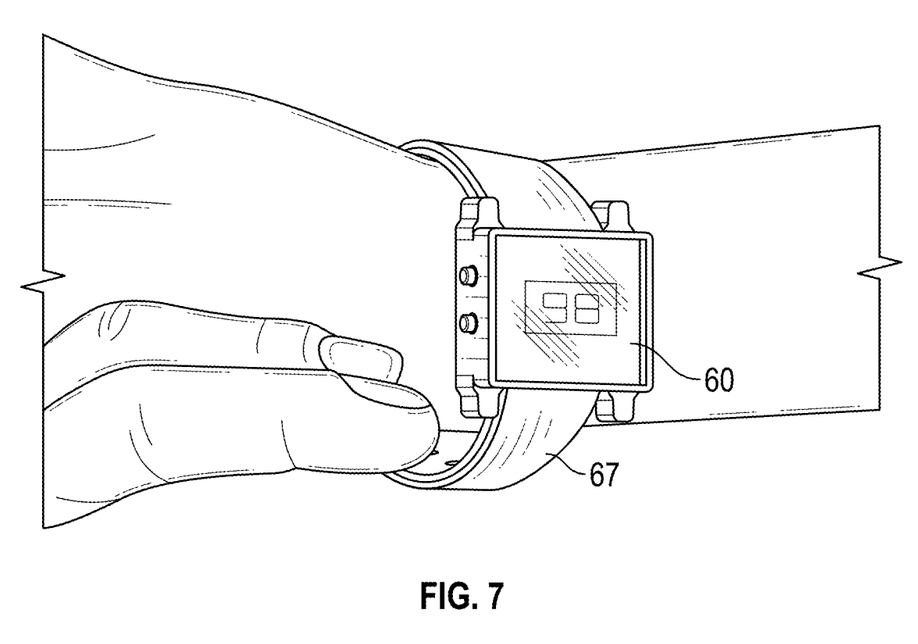
FIG. 7 illustrates the wristwatch being worn, prior to insertion of fingers under the watchband.

FIG. 7 illustrates an exemplary view of the watch 60, prior to insertion of two fingers from the opposing arm being placed under the watchband.

Figure 8:
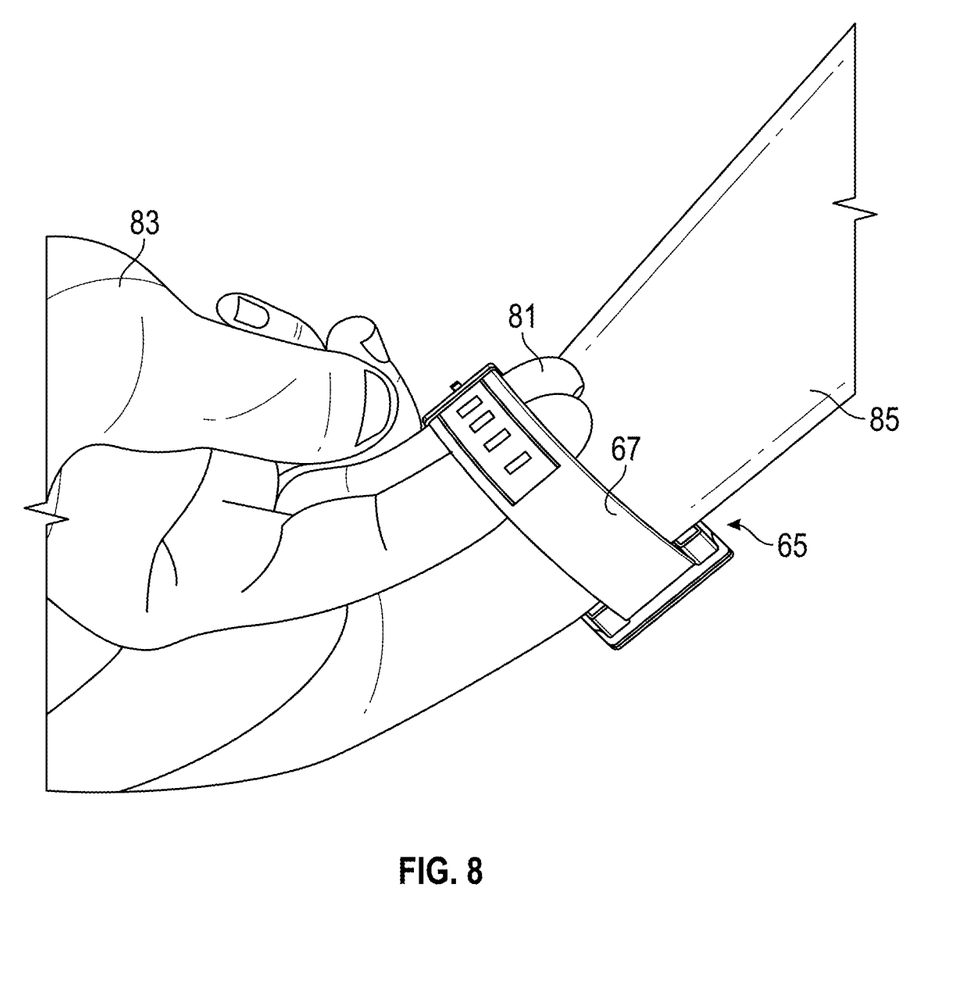
FIG. 8 illustrates an exemplary use of the wristwatch, with the second electrode being used.

FIG. 8 illustrates an exemplary view of two fingers 81 from one hand 83 of a first arm being placed under the watchband 67 located on the opposing arm 85.

Advantageously, the invention provides a method and apparatus that easily detect the presence of atrial fibrillation, and differentiates atrial fibrillation from non-atrial fibrillation rhythms including normal and other abnormal rhythms.

A still further advantage is that the invention provides relatively simple, non-invasive monitoring for long term at home or other location outside of a physician's office. Nevertheless, the use of the invention may occur at a physician's office or hospital or at any location where long term heart monitoring is desired.

Exemplary embodiments are provided below. It should be noted that any or all of these features may be used in combination thereof, and in combination with various features and components discussed above.

An embodiment of the invention includes a wearable apparatus for analyzing atrial fibrillation. The apparatus may include a housing. The housing may include a first electrode. The first electrode may be located on a surface of the housing. The first electrode may be located on an underside surface of the housing.

The apparatus may include a securing mechanism. The securing mechanism may secure the housing to a patient. The securing mechanism may secure the housing to a first appendage of a patient.

The apparatus may further include a second electrode. The second electrode may be located on a second surface of the securing mechanism. The second electrode may be configured to contact a second appendage. The contact between the second electrode and the second appendage may facilitate detection of an ECG signal.

The apparatus may further include a pulse detector. The pulse detector may be arranged in the housing. The pulse detector may be configured to obtain a pulse of the patient. The pulse may be obtained when the housing is secured by the securing mechanism to the patient.

The apparatus may further include a signaling mechanism. The signaling mechanism may be arranged on or within the housing. The signaling mechanism may be configured to signal indications to the patient.

The apparatus may further include a processor. The processor may be coupled to the pulse detector. The processor may be configured to obtain the pulse of the patient. The processor may be configured to indicate, via the signaling mechanism, that an electrocardiogram (ECG) is needed. The indication may be performed based on data obtained by the pulse detector.

The processor may be configured to perform a first stage of analysis to determine if pulse beats form an irregular pattern. The first stage may include detecting the pulse on the first appendage of a patient. The detecting may be performed using the pulse detector affixed to the first appendage. The pulse detector may perform the detecting in combination with the processor.

The processor may be configured to detect pulse rhythms. The pulse rhythms may be from a succession of time intervals. Each pulse rhythm may correspond to a respective interval of time between successive pulse beats of a sequence of the pulse beats. If the pulse beats form an irregular pattern in the first stage, the processor may be configured to indicate the presence of an irregular pulse.

The processor may be configured to perform a second stage of analysis to determine a presence of atrial fibrillation. The second stage may include the processor detecting the ECG signal simultaneously with pulse rhythms. The processor may analyze the detected pulse beats and the ECG signal. The analyzing may determine whether, in combination, the detected pulse beats and ECG signal are indicative of atrial fibrillation. The processor may be configured to provide an indication of atrial fibrillation when present. In the event atrial fibrillation is not present, the processor may be further configured to adjust the indication of the irregular pulse. The indication of irregular pulse may be adjusted based on the irregular pulse pattern detected in the second stage found to not be atrial fibrillation by analysis of the ECG signals in said second stage.

In an embodiment, the determination that atrial fibrillation is not present in the second stage may be performed by a human analysis of the said ECG signal.

An embodiment of the invention may include a wearable apparatus for analyzing atrial fibrillation. The apparatus may include a housing. The housing may include a first electrode located on an underside of its surface.

The apparatus may further include a securing mechanism. The securing mechanism may secure the housing to a first appendage of a patient. The apparatus may further include a second electrode. The second electrode may be located on an inside surface of the securing mechanism.

The apparatus may further include a signaling mechanism. The signaling mechanism may be arranged on the housing. The signaling mechanism may be configured to signal to the patient indications.

The apparatus may yet further include a processor. The processor may be configured to detect an ECG signal. The processor may be configured to analyze the detected ECG signal to determine whether it is indicative of atrial fibrillation. The processor may be configured to provide an indication of atrial fibrillation, when present.

In an embodiment, the first electrode may be in contact with a wrist. The first electrode may be in contact with skin of a wrist. In another embodiment, the skin in contact with the first electrode may be the skin upon which the wearable apparatus is worn.

In an embodiment, the securing mechanism may be a watchband. The watchband may be formed securely around the appendage.

In an embodiment, the ECG is recorded when at least one finger of the first appendage is placed between a wrist of the appendage and the securing mechanism. The at least one finger may include a second finger.

In an embodiment, the processor may be further configured to record the ECG when at least one finger from a second appendage is placed between the securing mechanism and the first appendage. The second appendage may not be wearing the apparatus. Then at least one finger from the second appendage may therefore contact the second electrode on an inside of the securing mechanism.

In an embodiment, the processor may be further configured to record the ECG only when at least one finger from a second appendage that is not wearing the apparatus is placed between the securing mechanism and the first appendage, such that the at least one finger from the second appendage may contact the second electrode on the underside of the securing mechanism.

In an embodiment, the processor may only be capable of detecting the ECG signal and providing an indication of atrial fibrillation when both the first and second appendages are in a relaxed position. In another embodiment, the processor may perform with increased accuracy and/or speed when both the first and second appendages are in a relaxed position.

In an embodiment, the processor is only capable of detecting the ECG signal and providing an indication of atrial fibrillation when a first hand and a second hand are in a relaxed position. In another embodiment, the processor may perform with increased accuracy and/or speed when a first hand and a second hand are in a relaxed position.

In an embodiment, continued contact between the apparatus and the first and second fingers may be provided at least in part due to a tension of the securing mechanism on the wrist of the first appendage and at least one finger from the second appendage.

In an embodiment, the securing mechanism may stretch to accommodate fingers from the second appendage.

In an embodiment, the first securing mechanism may further include a plurality of lugs. The lugs may be configured to be stretched so as to accommodate the at least one finger of the second appendage being placed between securing mechanism and the first appendage.

In an embodiment, the second electrode may be as large as the width of two fingers. The two fingers may be two average-sized fingers.

In an embodiment, the ECG may be configured to begin recording automatically when the securing mechanism is stretched past a preconfigured level.

In an embodiment, the ECG may be configured to begin recording automatically when the plurality of lugs are stretched past a preconfigured level.

An embodiment of the invention may include a wearable apparatus for analyzing atrial fibrillation. The apparatus may include a housing. The housing may include a first electrode. The first electrode may be located on an underside of a surface the housing.

The apparatus may include a securing mechanism. The securing mechanism may secure the housing to an appendage of a patient. The apparatus may include a pulse detector. The pulse detector may be arranged in the housing. The pulse detector may be configured to obtain a pulse of the patient. The pulse may be obtained when the housing is secured by the securing mechanism to the patient.

The apparatus may further include a mechanism. The mechanism may be located within the housing. The mechanism may be configured to determine when the appendage is stationary.

The apparatus may further include a signaling mechanism. The signaling mechanism may be arranged on or in the housing. The signaling mechanism may be configured to signal to the patient indications.

The apparatus may yet further include a processor. The processor may be coupled to the pulse detector. The processor may be configured to obtain the pulse of the patient. The processor may be configured to determine if pulse beats form an irregular pattern. The processor may be configured to detect the pulse on the first appendage of a patient using the pulse detector affixed to the first appendage.

The processor may be further configured to detect pulse rhythms from a succession of time intervals. Each pulse rhythm may correspond to a respective interval of time between successive pulse beats of a sequence of the pulse beats. The processor may therefore be configured to detect a series of pulse rhythms corresponding to respective time intervals between successive pulse beats, in a sequence of pulse beats.

The processor may be configured to determine if the pulse beats form an irregular pattern in the first stage. The processor may then indicate the presence of an irregular pulse.

In an embodiment, the pulse detection may occur only when the first appendage is stationary.

In an embodiment, the mechanism for determining if the appendage is stationary may be an accelerometer located in the housing.

In an embodiment, the apparatus may be configured to signal to the wearer, via the signaling mechanism, to keep the appendage stationary. The signal may be sent if the mechanism determines that the appendage has not been stationary during a fixed time period in which the pulse detection was to occur.

Additional information about heart monitoring and processing of heart signals is disclosed in U.S. Pat. Nos. 6,519,490, 7,020,514, 7,680,532 and 7,706,868, to the same inventor. The disclosures of all of these patents are incorporated by reference herein. Also, the techniques disclosed in these patents may be used in combination with or as modifications to the techniques disclosed herein, and such are also considered to be inventions Although the present invention has been described in relation to particular embodiments thereof, many other variations and modifications and other uses may become apparent to those skilled in the art. It is preferred, therefore, that the present invention be limited not by this specific disclosure herein, but only by the appended claims.

What is claimed is:

1. A method for modifying a detection of an irregular pulse beat via a wearable apparatus to rule out atrial fibrillation, comprising:
   providing:
      a housing with a plurality of electrodes to record an electrocardiogram (ECG);
      a pulse detector, the pulse detector configured to obtain a first pulse rhythm, a second pulse rhythm, and a third pulse rhythm; and
      a securing mechanism for securing said housing to an appendage of a patient;
   obtaining the first pulse rhythm;
   if the first pulse rhythm is determined to be irregular, initiating a second stage to determine a presence of atrial fibrillation, the second stage comprising:
      obtaining the first pulse rhythm and the ECG simultaneously; and
      determining, based on the ECG, if the first pulse rhythm is atrial fibrillation; and,
      if atrial fibrillation is not detected by the ECG, modifying the pulse detector, such that when obtaining the second and third pulse rhythms, the pulse detector comprises the steps of:
         not indicating, when detecting the second or third pulse rhythms that are substantially similar to the first rhythm detected via the second stage, the presence of an irregular rhythm; and
         affirmatively indicating, when the pulse detector detects the second or third pulse rhythms that are irregular and different than the first pulse rhythm detected via the second stage, the presence of the irregular rhythm.

2. The method of claim 1, wherein the second and third pulse rhythms are substantially similar to the first pulse rhythm only if all pulse rhythms indicate a pattern of premature beats.

3. The method of claim 1, wherein the second and third pulse rhythms are different than the first pulse rhythm only if the first pulse rhythm indicates a pattern of premature beats, but the second and third pulse rhythms do not indicate the pattern of premature beats.

4. The method of claim 1, wherein a final determination that atrial fibrillation is not present in the second stage is manually input.

5. The method of claim 1, further comprising securing the wearable apparatus to a first appendage.

6. The method of claim 5, the obtaining the ECG further comprising placing at least one finger from a second appendage underneath the securing mechanism.

7. The method of claim 6, wherein the securing mechanism includes a plurality of lugs, the method further comprising stretching the lugs to accommodate at least one finger of the second appendage being placed between the securing mechanism and the first appendage.

8. The method of claim 1, wherein the plurality of electrodes includes a first electrode and a second electrode, the second electrode being at least as large as the width of two fingers.

9. The method of claim 1, wherein the obtaining the ECG further comprises the ECG beginning recording automatically when the seeming mechanism is stretched past a preconfigured level.

10. The method of claim 1, wherein the obtaining the ECG further comprises the ECG beginning recording automatically when the plurality of lugs are stretched past a preconfigured level.

11. A method for modifying a detection of an irregular pulse beat via a wearable apparatus to rule out atrial fibrillation, comprising:
   providing:
      a housing with a plurality of electrodes to record an electrocardiogram (ECG);
      a pulse detector, the pulse detector configured to obtain a first pulse rhythm and a plurality of subsequent pulse rhythms; and
      a securing mechanism for securing said housing to an appendage of a patient;
   obtaining the first pulse rhythm;
   if the first pulse rhythm is determined to be irregular, initiating a second stage to determine a presence of atrial fibrillation, the second stage comprising:
      obtaining the first pulse rhythm and the ECG simultaneously; and
      determining, based on the ECG, if the first pulse rhythm is atrial fibrillation;
   if atrial fibrillation is not detected by the ECG, modifying the pulse detector such that when obtaining all subsequent pulse rhythms, the pulse detector comprises the steps of:
      not indicating the presence of an irregular rhythm when the pulse detector detects subsequent pulse rhythms that are substantially similar to the first pulse rhythm that was detected; and
      affirmatively indicating the presence of an irregular rhythm only when the pulse detector detects subsequent pulse rhythms that are both irregular and different than the first pulse rhythm that was detected.

12. The method of claim 11, wherein the subsequent pulse rhythms are substantially similar to the first pulse rhythm only if all the pulse rhythms indicate a pattern of premature beats.

13. The method of claim 11, wherein the subsequent pulse rhythms are substantially different than the first pulse rhythm only if the first pulse rhythm indicates a pattern of premature beats, but the subsequent pulse rhythms do not indicate the pattern of premature beats.

14. The method of claim 11, wherein a final determination that atrial fibrillation is not present in the second stage is manually input.

15. The method of claim 11, further comprising securing the wearable apparatus to a first appendage, and the obtaining the ECG further comprising placing at least one finger from a second appendage underneath the securing mechanism.

16. The method of claim 15, wherein the securing mechanism includes a plurality of lugs, the method further comprising stretching the lugs to accommodate at least one finger of the second appendage being placed between the securing mechanism and the first appendage.

17. The method of claim 11, wherein the plurality of electrodes includes a first electrode and a second electrode, the second electrode being at least as large as the width of two fingers.

18. The method of claim 11, wherein the obtaining the ECG further comprises the ECG beginning recording automatically when the securing mechanism is stretched past a preconfigured level.

19. The method of claim 11, wherein the obtaining the ECG further comprises the ECG beginning recording automatically when the plurality of lugs are stretched past a preconfigured level.

20. A method for modifying a detection of an irregular pulse beat via a wearable apparatus to rule out atrial fibrillation, comprising:
   providing:
      a housing with a plurality of electrodes to record an electrocardiogram (ECG);
      a pulse detector, the pulse detector configured to obtain a first pulse rhythm and a plurality of subsequent pulse rhythms; and
      a securing mechanism for securing said housing to an appendage of a patient;
   obtaining the first pulse rhythm;
   if the first pulse rhythm is determined to be irregular, initiating a second stage to determine a presence of atrial fibrillation, the second stage comprising:
      obtaining the first pulse rhythm and the ECG simultaneously; and
      determining, based on the ECG, if the first pulse rhythm is atrial fibrillation;
   if atrial fibrillation is not detected by the ECG, determining, via the ECG, whether premature beats are present; and
   if premature beats are present, modifying the pulse detector such that, when obtaining all subsequent pulse rhythms, the pulse detector does not indicate the presence of an irregular rhythm if premature beats are detected by the pulse detector.

* * * * *